US00PP14995P2

(12) United States Plant Patent
Van Andel

(10) Patent No.: US PP14,995 P2
(45) Date of Patent: Jul. 6, 2004

(54) NEPHROLEPIS PLANT NAMED 'NR.21'

(50) Latin Name: *Nephrolepis exaltata*
Varietal Denomination: Nr.21

(75) Inventor: Otto Jan Robert Van Andel, De Kwakel (NL)

(73) Assignee: Braam Young Plants B.V., DeKwakel (NL)

( * ) Notice: Subject to any disclaimer, the term of this patent is extended or adjusted under 35 U.S.C. 154(b) by 0 days.

(21) Appl. No.: 10/716,058

(22) Filed: Nov. 18, 2003

(51) Int. Cl.[7] ..... A01H 5/00
(52) U.S. Cl. ..... Plt./379
(58) Field of Search ..... Plt./379

*Primary Examiner*—Bruce R. Campell
*Assistant Examiner*—Annette H Para
(74) *Attorney, Agent, or Firm*—C. A. Whealy

(57) ABSTRACT

A new and distinct cultivar of Nephrolepis plant named 'Nr. 21', characterized by its mostly upright and somewhat outwardly arching plant habit; strong, erect and visible rachis; and long straight fronds with numerous undulate pinnae.

1 Drawing Sheet

Botanical classification: *Nephrolepis exaltata* cultivar Nr. 21.

BACKGROUND OF THE INVENTION

The present invention relates to a new and distinct cultivar of Nephrolepis fern plant, botanically known as *Nephrolepis exaltata,* and hereinafter referred to by the name 'Nr. 21'.

The new Nephrolepis fern is a naturally-occurring whole plant mutation of the *Nephrolepis exaltata* cultivar Whitmanii, not patented. The new Nephrolepis fern was discovered by the Inventor in a controlled environment in De Kwakel, The Netherlands in November, 2000.

Since May 2001, asexual reproduction by divisions of the new Nephrolepis fern in a controlled environment at De Kwakel, The Netherlands has shown that the unique features of this new Nephrolepis fern are stable and retained through successive generations of asexual reproduction.

SUMMARY OF THE INVENTION

The new Nephrolepis fern has not been observed under all possible environmental conditions. The phenotype may vary somewhat with variations in environment such as temperature and light intensity without, however, any variance in genotype. The following observations, measurements and comparisons describe plants grown in De Kwakel, The Netherlands, under conditions generally used in commercial practice.

The following traits have been repeatedly observed and are determined to be the unique characteristics of 'Nr. 21'. These characteristics in combination distinguish 'Nr. 21' as a new and distinct cultivar:

1. Mostly upright and somewhat outwardly arching plant habit.
2. Strong, erect and visible rachis.
3. Long straight fronds with numerous undulate pinnae.

The new Nephrolepis fern is most similar to its parent cultivar, the *Nephrolepis exaltata* cultivar Whitmanii. However in side-by-side comparisons conducted in De Kwakel, The Netherlands, the new Nephrolepis fern differed from plants of the cultivar Whitmanii in the following characteristics:

1. Plants of the new Nephrolepis fern were more upright in plant habit than plants of the cultivar Whitmanii.
2. Plants of the new Nephrolepis fern were more compact than plants of the cultivar Whitmanii.
3. Plants of the new Nephrolepis fern had narrower fronds than plants of the cultivar Whitmanii.

The new Nephrolepis fern can be compared to plants of the *Nephrolepis exaltata* cultivar Corditas, not patented. However in side-by-side comparisons conducted in De Kwakel, The Netherlands, the new Nephrolepis fern differed from plants of the cultivar Corditas in the following characteristics:

1. Plants of the new Nephrolepis fern were more upright in plant habit than plants of the cultivar Corditas.
2. Plants of the new Nephrolepis fern had longer fronds than plants of the cultivar Corditas.
3. Rachis of plants of the new Nephrolepis were more visible than rachis of plants of the cultivar Corditas.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Nephrolepis fern.

The photograph at the top of the first sheet comprises a side perspective view of a typical plant of 'Nr. 21'.

The photograph at the bottom of the sheet comprises a close-up view of a typical frond of 'Nr. 21'.

DETAILED BOTANICAL DESCRIPTION

In the following description, color references are made to The Royal Horticultural Society Colour Chart, 2001 Edition, except where general terms of ordinary dictionary significance are used.

Plants in the aforementioned photographs and used in the following description were grown under conditions which closely approximate commercial production conditions from February to June in a glass-covered greenhouse in De Kwakel, The Netherlands. During the production of the plants, day temperatures were about 22° C., night temperatures were about 19° C. and light levels were about 22,000 to 28,000 lux. Plants in the photographs and used for the description were about six months old when the photographs and description were taken.

In the following description, color references are made to The Royal Horticultural Society Colour Chart, 2001 Edition, except where general terms of ordinary dictionary significance are used.

Botanical classification: *Nephrolepis exaltata* cultivar Nr. 21.

Parentage: Naturally-occurring whole plant mutation of *Nephrolepis exaltata* cultivar Whitmanii, not patented.

Propagation: By tissue culture.

Propagation:

*Time to initiate roots, summer.*—About 30 days at 24° C.

*Time to initiate roots, winter.*—About 35 days at 22° C.

*Root description.*—Fine and brown in color.

Plant description:

*Growth habit.*—Mostly upright and somewhat outwardly arching; symmetrical; relatively compact; appropriate for 10 to 15-cm containers.

*Plant height.*—About 50 to 60 cm from soil line to top of plant plane.

*Plant width.*—About 85 cm.

*Plant vigor.*—Moderate.

*Frond description.*—Quantity of fronds per plant: About 100. Leaf arrangement: Bi-pinnate. Frond length: About 30 to 60 cm. Frond width: About 3 to 7 cm. Rachis length: About 30 to 60 cm. Rachis diameter: About 1.5 to 2.5 mm. Rachis color: 146A overlain with 186A.

*Pinnae description.*—Shape: Narrowly deltoid. Length: About 5 to 17 mm. Width: About 2 to 8 mm. Quantity of pinnae: Numerous, about 400 to 500 per frond. Margin: Slightly dentate; undulate. Apex: Acute. Base: Truncate, asymmetrical. Aspect: Undulate along axis. Attachment: Sessile. Texture: Leathery; glabrous. Venation pattern: Pinnate. Color: When developing, upper and lower surfaces: 144B. Fully developed, upper surface: Between 143A and 137A; venation, 146A. Fully developed, lower surface: Between 143A and 137C; midvein, 146A, lateral veins, 146B.

*Spores.*—None observed.

Disease/pest resistance: Resistance to pathogens and pests common to Nephrolepis ferns has been observed.

Temperature tolerance: Plants of the new Nephrolepis fern have been observed to be tolerant to temperatures ranging from 12 to 32° C.

It is claimed:

1. A new and distinct cultivar of Nephrolepis plant named 'Nr. 21', as illustrated and described.

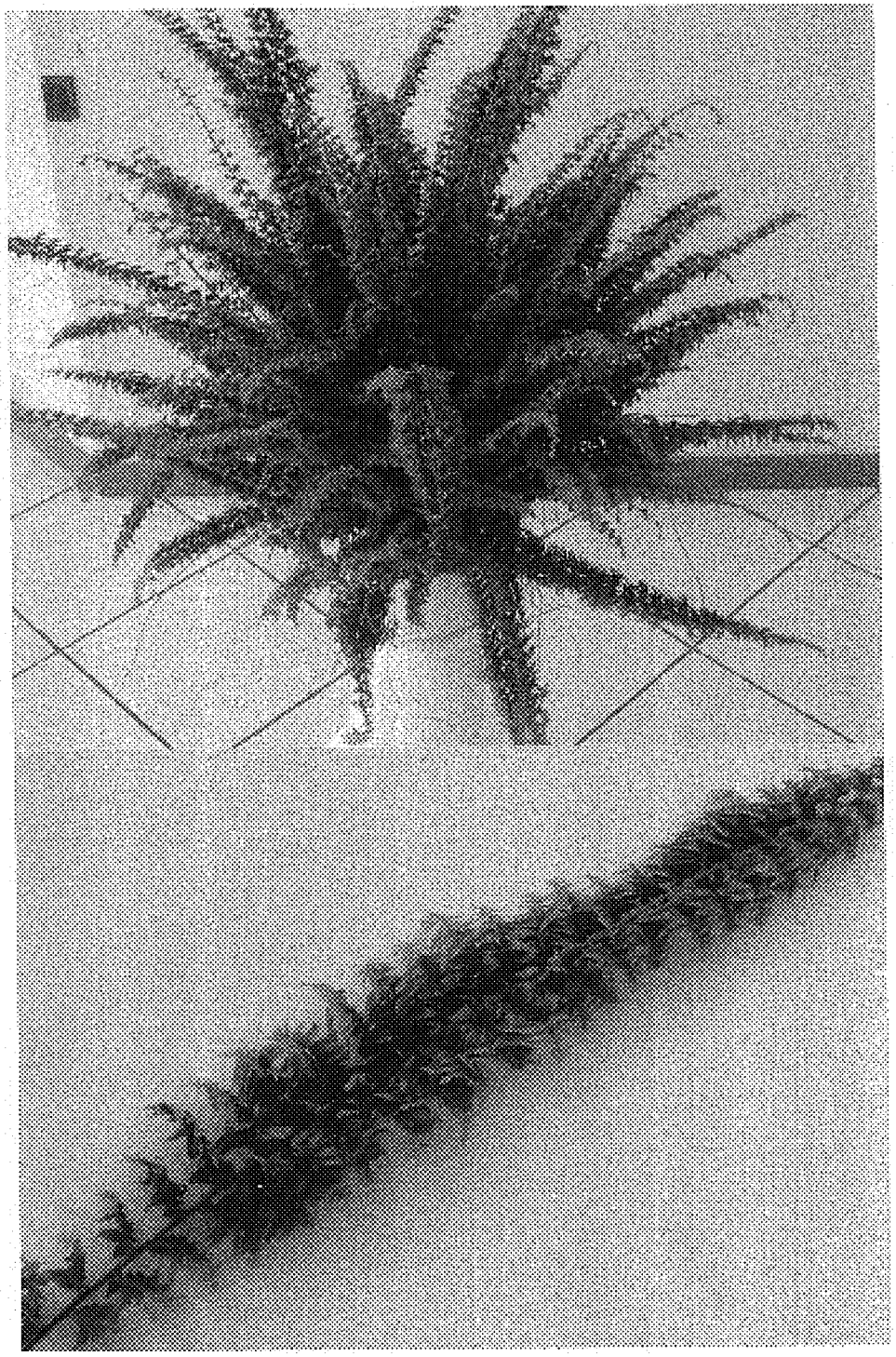

* * * * *